United States Patent [19]
Cochran et al.

[11] Patent Number: 5,243,084
[45] Date of Patent: Sep. 7, 1993

[54] OXIDATION OF ISOBUTANE TO TERTIARY BUTYL HYDROPEROXIDE

[75] Inventors: Robert N. Cochran; Shaw-Chan Lin, both of West Chester, Pa.

[73] Assignee: ARCO Chemical Technology, L.P., Wilmington, Del.

[21] Appl. No.: 992,395

[22] Filed: Dec. 17, 1992

Related U.S. Application Data

[63] Continuation-in-part of Ser. No. 872,794, Apr. 22, 1992, Pat. No. 5,196,597.

[51] Int. Cl.$^5$ .................. C07C 409/04; C07C 407/00
[52] U.S. Cl. .................. 568/571; 568/569; 568/910; 568/910.5
[58] Field of Search .................. 568/909.8, 569, 571, 568/910, 910.5, 570, 572

[56] References Cited

U.S. PATENT DOCUMENTS

| | | | |
|---|---|---|---|
| 2,845,461 | 7/1958 | Winkler et al. | 568/571 |
| 3,351,635 | 11/1967 | Kollar | 568/571 |
| 3,478,108 | 11/1969 | Grane | 568/571 |
| 3,907,902 | 9/1975 | Grane | 568/571 |
| 4,404,406 | 9/1983 | Lutz | 568/571 |
| 4,408,081 | 5/1986 | Foster et al. | 568/571 |
| 4,408,082 | 10/1986 | Baumgartner | 568/571 |
| 5,151,530 | 9/1992 | Marquis et al. | 568/571 |
| 5,162,593 | 11/1992 | Maffia et al. | 568/909.8 |

OTHER PUBLICATIONS

Winkler et al "Ind. & Eng. Chem.", vol. 53, No. 8, pp. 655–658, Apr. 5, 1993.

Primary Examiner—Werren B. Lone
Attorney, Agent, or Firm—William C. Long

[57] ABSTRACT

The present invention relates to a process for the oxidation of isobutane in the liquid phase to produce TBA and TBHP wherein at least a portion of the oxidation product mixture is obtained as distillate from fractional distillation of vapors from the oxidation zone.

3 Claims, 1 Drawing Sheet

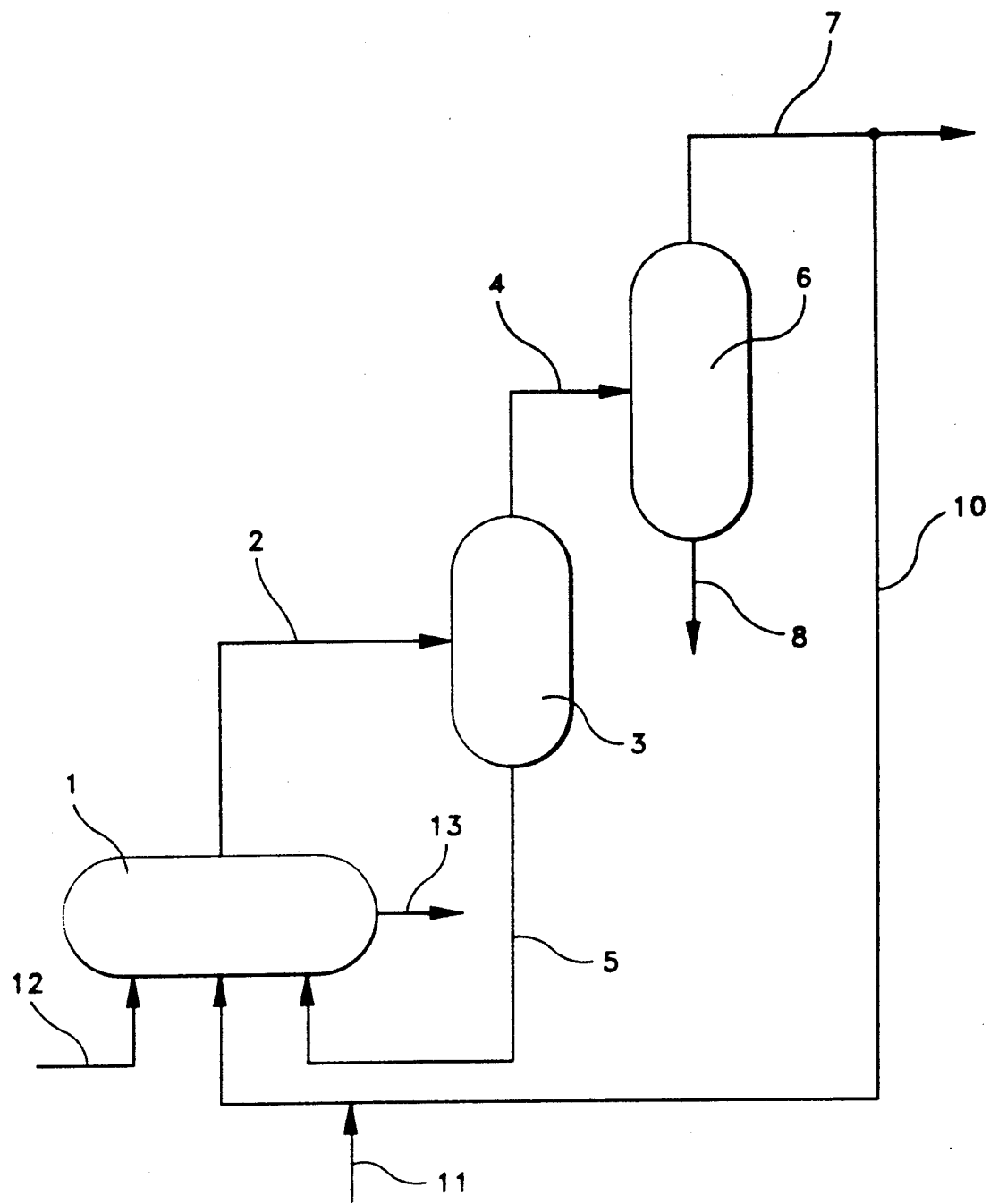

OXIDATION OF ISOBUTANE TO TERTIARY BUTYL HYDROPEROXIDE

BACKGROUND OF THE INVENTION

Related Application

The present application is a continuation-in-part of allowed copending application Ser. No. 07/872,794 filed Apr. 22, 1992, now U.S. Pat. No. 5,196,597.

Field of the Invention

The present invention relates to the oxidation of isobutane to tertiary butyl hydroperoxide (TBHP) and tertiary butyl alcohol (TBA) and to an improved method for carrying out the oxidation wherein at least a portion of the net oxidation product is obtained by distillation of vapors from the oxidation zone.

Description of the Prior Art

Methods are known for the production of TBHP by the molecular oxygen oxidation of isobutane at elevated temperature and pressure. In this regard, attention is drawn to U.S. Pat. No. 2,845,461 of Winkler, et al., to U.S. Pat. No. 3,478,108 of Grane and to U.S. Pat. No. 4,408,081 of Foster, et al. Frequently, the TBHP product from the oxidation is used to epoxidize olefins such as propylene by procedures such as those described in basic U.S. Pat. No. 3,351,635.

Problems associated with prior processes have been lower than desired reaction rates and greater than desired make of by-products. In addition, in some situations, due to fluctuation in market conditions, it is advantageous to produce more tertiary butyl alcohol (TBA) relative to the amount of epoxide which is formed by reaction of TBHP with olefin.

In the process of said copending application Ser. No. 07/872,794 filed Apr. 22, 1992, the amount of TBA produced relative to TBHP is increased by recovering at least a portion of the TBA and TBHP condensate of the vapors removed from the oxidation zone as an oxidation product stream.

In accordance with the present invention, a straightforward and simple method is provided for further improving the amount of TBA produced relative to TBHP which is readily applicable to existing commercial practice.

BRIEF DESCRIPTION OF THE INVENTION

In practice of the present invention, isobutane is oxidized in the liquid phase with molecular oxygen to form tertiary butyl hydroperoxide (TBHP) as well as tertiary butyl alcohol (TBA) in accordance with known and conventional procedures. During the process, a vapor mixture comprised of unreacted oxygen, inerts, isobutane, TBHP and TBA is removed from the oxidation reaction zone and passed to a fractional distillation zone from which a product stream further enriched in TBA relative to TBHP is recovered and a stream enriched in TBHP relative to TBA is returned to the oxidation zone.

DESCRIPTION OF THE DRAWING

The accompanying drawing illustrates in schematic form practice of the invention.

DETAILED DESCRIPTION

The invention can best be described with reference to the accompanying drawing. Referring to the drawing, isobutane is reacted with oxygen in reactor 1 to produce TBHP along with TBA. The isobutane oxidation reaction conditions in oxidation reactor 1 are those which are normally used for this reaction as described, for example, in Winkler, et al. U.S. Pat. No. 2,845,461. Generally, reaction temperatures in the range of 100° C. to 200° C., preferably 120° C. to 150° C. are employed. Pressures in the range of 200 to 500 psig, preferably 300 to 450 psig are employed. Residence times in the oxidation zone of 3 to 15 hours, preferably 5 to 10 hours are suitable. It is preferred to use oxygen as the oxidant, although the use of oxygen in admixture with minor amounts of an inert gas such as nitrogen can be used.

As a result of the isobutane oxidation in reaction zone 1, both TBHP and TBA are produced. Generally, the weight ratio of TBA to TBHP produced in reaction zone 1 is less than 0.8. In order to remove the exothermic heat of reaction, conditions of the reaction in zone 1 are regulated such that the reaction mixture is constantly boiling with vapors being removed from zone 1 by means of line 2. Vaporization results in the removal of the exothermic heat of reaction.

The weight ratio of TBA to TBHP in the vapors which are removed from zone 1 is generally above about 1.0 due to the relative boiling points of these materials. Also contained in the vapor stream from zone 1 is unreacted isobutane, unreacted molecular oxygen and inert materials.

In accordance with the invention, the vapors from zone 1 pass via line 2 to fractional distillation zone 3. In zone 3 components of the vapor mixture from zone 1 are fractionally distilled, and an overhead fraction comprised of isobutane together with TBA and TBHP is separated via line 4 and passes to fractional distillation zone 6. This vapor stream passing from zone 3 to zone 6 via line 4 is more concentrated in TBA relative to TBHP than is the vapor stream exiting zone 1 via line 2 or the liquid reaction mixture in zone 1.

A liquid bottoms stream comprised of TBA and TBHP is removed from distillation zone 3 via line 5 and recycled to oxidation zone 1. This bottoms stream is more concentrated in TBHP relative to TBA than is the vapor mixture exiting zone 1 via line 2.

In zone 6 the vapor mixture from zone 3 is further fractionally distilled, and a vapor fraction comprised of isobutane and other light components is separated as overhead via line 7. A portion is recycled to oxidation zone 1 via line 10 and a portion is purged via line 9.

A liquid distillate stream is recovered from zone 6 via line 8 and comprises a net product of the oxidation. This stream comprises TBA and TBHP and is more concentrated in TBA relative to TBHP than is the vapor stream exiting zone 1 via line 2 or the liquid reaction mixture in zone 1, i.e. the TBA/TBHP weight ratio is more than 1.0 and is higher than the same ratio in the vapor stream from zone 1.

Depending on the particular economics of a practice of the invention, the net product stream recovered via line 8 can comprise from about at least 5% to as high as 95% of the total net TBA and TBHP recovered from zone 1.

Molecular oxygen is introduced into oxidation zone 1 by means of lines 11 and 10 and fresh and recycled isobutane is fed to zone 1 via lines 12 and 10.

Liquid oxidation product from zone 1 can be recovered by means of line 13, and this product together with the distillate recovered via line 8, comprises the overall liquid product of the oxidation taking place in zone 1.

In accordance with the invention, the vapors from zone 1 can be fractionally distilled in one or a plurality of fractional distillation zones having at least one theoretical stage. Depending upon the degree of separation desired, multi-stage fractional distillation configurations can be employed.

Practice of the present invention has some important advantages when contrasted with the procedures of the prior art and with the process of Ser. No. 07/872,794. The rate of oxidation and the selectivity of the oxidation to the desired TBA product is significantly improved as a result of the process. In addition, practice of the present invention provides added flexibility in the determination of the relative amounts of TBA and TBHP which are produced by the oxidation. This latter feature is of special significance since the TBHP normally is employed in the production of an epoxide such as propylene oxide. The added flexibility achieved by this process enables the overall process to be practiced more economically depending on the economic requirements at any particular time. By fractional distillation of the mixture separated as vapor from zone 1, the concentration of TBA in the recovered distillate stream is significantly increased relative to TBHP and the overall product ratio of these compounds can be varied as desired within fairly wide ranges to meet particular economic circumstances.

To further illustrate the invention, the following example is presented based on the process described in the attached drawing.

Isobutane in the amount of 89,340 lbs./hr. representing net fresh isobutane is introduced into reaction zone 1 by means of line 12. Molecular oxygen in amount of 16,100 lbs./hr. is introduced into zone 1 by means of line 11, the molecular oxygen representing >99% of this stream, the remainder being inerts which are primarily nitrogen.

The oxidation conditions maintained in zone 1 are a temperature of 137° C. and a pressure of 331 psig. Continuously removed from zone 1 via line 2 is a vapor mixture comprised of 57.4 wt. % isobutane, 19.7 wt. % TBA and 16.5 wt. % TBHP. This stream is removed at the rate of 595,840 lbs./hr. and passes to fractionation zone 3 which is a single-stage fractionation column. Overhead vapors at 124° C. and 330 psig and having a composition by weight of 67.3% isobutane, 15.7% TBA and 9.5% TBHP are separated at the rate of 338,800 lbs./hr. via line 4 and pass to fractionation zone 6.

A bottoms stream is recovered from zone 3 via line 5 and is recycled to zone 1 at the rate of 257,030 lbs./hr. The composition of this stream by weight is 25.6% TBHP, 25.1% TBA and 44.3% isobutane.

Zone 6 is a single-stage fractionation column. Overhead vapor at 116° C. and 330 psig and having a composition by weight of 72.8% isobutane, 12.7% TBA and 6.0% TBHP is removed at the rate of 251,210 lb./hr. via line 7. A portion of this stream in amount of 3,660 lb./hr. is purged via line 9 with the remainder being recycled via line 10 to zone 1.

A liquid stream is removed from zone 6 via line 8 at the rate of 87,600 lb./hr. as a product of the oxidation process. The composition by weight of this stream is 51.5% isobutane, 24.1% TBA, and 19.8% TBHP.

A liquid oxidation reaction mixture stream having the composition by weight 25.2% TBA, 33.0% TBHP and 34.6% isobutane is removed from zone 1 via line 13 at the rate of 16,070 lbs./hr. and also represents a product of the oxidation process.

From the above it can be seen that the TBA to TBHP weight ratio in the product stream recovered from column 6 is significantly higher than that of the liquid stream from reactor 1. In addition, the reaction rate is substantially improved and the make of undesirable by-products is substantially less as contrasted with conventional procedures.

We claim:

1. The process for the oxidation of isobutane to produce tertiary butyl alcohol and tertiary butyl hydroperoxide wherein isobutane is reacted with molecular oxygen in the liquid phase at 100°-200° C., a vapor stream comprised of tertiary butyl alcohol and tertiary butyl hydroperoxide is continuously removed during the oxidation from the oxidation zone and fractionally distilled, ad a distillate comprised of tertiary butyl alcohol and tertiary butyl hydroperoxide and enriched in tertiary butyl alcohol relative to tertiary butyl hydroperoxide is recovered.

2. The process of claim 1 wherein the recovered distillate enriched in tertiary butyl alcohol relative to tertiary butyl hydroperoxide comprises 5 to 95% of the total net tertiary butyl alcohol and tertiary butyl hydroperoxide recovered from the oxidation.

3. The process of claim 1 wherein the weight ratio of tertiary butyl alcohol to tertiary butyl hydroperoxide in the recovered distillate enriched in tertiary butyl alcohol relative to tertiary butyl hydroperoxide is above about 1.0.

* * * * *